(12) United States Patent
Sanford et al.

(10) Patent No.: US 11,059,782 B2
(45) Date of Patent: Jul. 13, 2021

(54) METHOD FOR AROMATIC FLUORINATION

(71) Applicants: DOW GLOBAL TECHNOLOGIES LLC, Midland, MI (US); THE REGENTS OF THE UNIVERSITY OF MICHIGAN, Ann Arbor, MI (US)

(72) Inventors: Melanie S. Sanford, Ann Arbor, MI (US); Megan A. Cismesia, Midland, MI (US); Patrick S. Hanley, Midland, MI (US); Douglas Bland, Midland, MI (US)

(73) Assignees: Dow Global Technologies LLC, Midland, MI (US); The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 16/317,336

(22) PCT Filed: Jul. 13, 2017

(86) PCT No.: PCT/US2017/041889
§ 371 (c)(1),
(2) Date: Jan. 11, 2019

(87) PCT Pub. No.: WO2018/013782
PCT Pub. Date: Jan. 18, 2018

(65) Prior Publication Data
US 2019/0292152 A1    Sep. 26, 2019

Related U.S. Application Data

(60) Provisional application No. 62/362,725, filed on Jul. 15, 2016.

(51) Int. Cl.
| | | |
|---|---|---|
| *C07D 213/30* | (2006.01) | |
| *C07B 39/00* | (2006.01) | |
| *C07C 49/215* | (2006.01) | |
| *C07C 211/63* | (2006.01) | |
| *C07D 221/04* | (2006.01) | |
| *C07D 215/18* | (2006.01) | |
| *C07C 45/63* | (2006.01) | |
| *C07C 45/61* | (2006.01) | |
| *C07D 213/79* | (2006.01) | |

(52) U.S. Cl.
CPC ............ *C07D 213/30* (2013.01); *C07B 39/00* (2013.01); *C07C 45/61* (2013.01); *C07C 45/63* (2013.01); *C07C 49/215* (2013.01); *C07C 211/63* (2013.01); *C07D 213/79* (2013.01); *C07D 215/18* (2013.01); *C07D 221/04* (2013.01)

(58) Field of Classification Search
CPC ............................. C07C 211/62; C07C 211/63
See application file for complete search history.

(56) References Cited

U.S. PATENT DOCUMENTS 9,150,516 B2    10/2015    Ritter et al.

FOREIGN PATENT DOCUMENTS

| WO | 2011/008725 | 1/2011 | |
| WO | WO-2011008725 A2 * | 1/2011 | ............ C07C 25/22 |
| WO | 2013188554 | 12/2013 | |

OTHER PUBLICATIONS

The International Search Report (ISR) with Written Opinion for PCT/US2017/041889 dated Oct. 9, 2017, pp. 1-12.
First Examination Report for Indian Patent Application No. 201917001390, dated Nov. 13, 2020, pp. 1-4.

* cited by examiner

*Primary Examiner* — John S Kenyon
(74) *Attorney, Agent, or Firm* — McDonnell Boehnen Hulbert & Berghoff LLP

(57) ABSTRACT

Disclosed is a fluorination method comprising providing a fluorinating reagent and a solvent to a reaction mixture; providing a compound having the formula Ar—X to the reaction mixture; wherein Ar is aryl, substituted aryl, heteroaryl or substituted heteroaryl, and X is Cl, Br, I or $NO_2$, providing tetramethylammonium 2,6-dimethylphenolate to the reaction mixture; and reacting under conditions sufficient to provide a species having the formula Ar—F.

17 Claims, No Drawings

METHOD FOR AROMATIC FLUORINATION

CROSS-REFERENCE TO RELATED APPLICATIONS

This application is a U.S. national phase of International Application No. PCT/US2017/041889, filed Jul. 13, 2017, which claims the benefit of priority to U.S. Provisional Application No. 62/362,725, filed Jul. 15, 2016, the disclosure of which is incorporated herein in its entirety.

BACKGROUND

Selectively fluorinated aromatic compounds having a carbon-fluorine (C—F) bond are often biologically active and can be used as active components of many drugs and agrochemicals. A common strategy for the formation of these C—F bonds is through nucleophilic aromatic substitution by replacing aryl-X bond, where X is, for example, Cl, Br, $NO_2$.

An improved method for fluorinating aromatic compounds is desired.

SUMMARY

In a broad aspect, this disclosure provides a method for preparing aryl fluorides, the method comprising forming a reaction mixture comprising a fluorinating reagent and a compound having the formula Ar—X, wherein Ar is aryl, substituted aryl, heteroaryl or substituted heteroaryl, and X is Cl, Br, I or $NO_2$, optionally in a solvent system; and providing tetramethylammonium 2,6-dimethylphenolate to the reaction mixture. The mixture is then allowed to react under conditions sufficient to provide a species having the formula Ar—F, after which the desired product may be isolated.

A fluorination method comprising providing a fluoride fluorinating reagent and a solvent to a reaction mixture; providing a compound having the formula Ar—X to the reaction mixture; wherein Ar is aryl, substituted aryl, heteroaryl or substituted heteroaryl, and X is Cl, Br, I or $NO_2$, providing tetramethylammonium 2,6-dimethylphenolate to the reaction mixture; and reacting under conditions sufficient to provide a species having the formula Ar—F.

DETAILED DESCRIPTION

"Alkyl," as used in this specification, whether alone or as part of another group (e.g., in dialkylamino), encompasses straight, cyclic and branched chain aliphatic groups having the indicated number of carbon atoms. If no number is indicated (e.g., aryl-alkyl-), then 1-12 alkyl carbons are contemplated. Preferred alkyl groups include, without limitation, methyl, ethyl, propyl, isopropyl, butyl, isobutyl, sec-butyl, tert-butyl, pentyl, hexyl and tert-octyl.

The term "heteroalkyl" refers to an alkyl group as defined above with one or more heteroatoms (nitrogen, oxygen, sulfur, phosphorus) replacing one or more carbon atoms within the radical, for example, an ether or a thioether.

An "aryl" group refers to any functional group or substituent derived from an aromatic ring. In one instance, aryl refers to an aromatic moiety comprising one or more aromatic rings. In one instance, the aryl group is a $C_6$-$C_{18}$ aryl group. In one instance, the aryl group is a $C_6$-$C_{10}$ aryl group. In one instance, the aryl group is a $C_{10}$-$C_{18}$ aryl group. Aryl groups contain 4n+2 pi electrons, where n is an integer. The aryl ring may be fused or otherwise attached to one or more heteroaryl rings, aromatic or non-aromatic hydrocarbon rings or heterocycloalkyl rings. Preferred aryls include, without limitation, phenyl, naphthyl, anthracenyl, and fluorenyl. Unless otherwise indicated, the aryl group is optionally substituted with 1 or more substituents that are compatible with the syntheses described herein. Such substituents include, but are not limited to:

sulfonate groups,
boron-containing groups,
alkyl groups,
nitro groups,
halogens,
cyano groups,
—C(O)$R_A$ where $R_A$ represents hydroxy, alkyl, alkoxy, aryl, aryloxy, heteroaryl, heteroaryloxy, amino, or mono- or di(alkylamino),
—$NR_N C(O)R_M$ where $R_N$ is H or alkyl and $R_M$ alkyl, aryl, or heteroaryl, $C_2$-$C_8$ alkenyl, and
other aromatic groups.
Other substituents are known in the art.

"Heteroaryl" refers to any functional group or substituent derived from an aromatic ring and containing at least one heteroatom selected from nitrogen, oxygen, and sulfur. Preferably, the heteroaryl group is a five or six-membered ring. The heteroaryl ring may be fused or otherwise attached to one or more heteroaryl rings, aromatic or non-aromatic hydrocarbon rings or heterocycloalkyl rings. Examples of heteroaryl groups include, without limitation, pyridinyl, pyrimidinyl, pyridazinyl, pyrrolyl, triazinyl, imidazolyl, triazolyl, furanyl, thienyl, oxazolyl, and thiazolyl. The heteroaryl group may be optionally substituted with one or more substituents that are compatible with the syntheses described herein. Such substituents include, but are not limited to:

fluorosulfonate groups,
sulfonate groups,
boron-containing groups,
alkyl groups,
nitro groups,
halogens,
cyano groups,
—C(O)$R_A$ where $R_A$ represents hydroxy, alkyl, alkoxy, aryl, aryloxy, heteroaryl, heteroaryloxy, amino, or mono- or di(alkylamino),
—$NR_N C(O)R_M$ where $R_N$ is H or alkyl and $R_M$ alkyl, aryl, or heteroaryl, $C_2$-$C_8$ alkenyl, and
other aromatic groups
Other substituents are known in the art.

"Alkoxy" refers to any functional group or substituent have an ether component and may include straight chain, branched, or cyclo alkyl, aromatic, heteroaromatic, or perfluoroalkyl substituents.

The present disclosure describes an improved method of fluorinating aromatic compounds having the formula Ar—X, wherein Ar is aryl, substituted aryl, heteroaryl or substituted heteroaryl, and X is Cl, Br, I or $NO_2$. The method can be represented by Scheme I below:

(Scheme I)

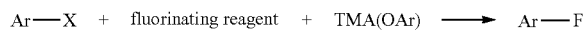

This method is performed in a reaction mixture. The reaction mixture comprises a fluoride fluorinating reagent, an optional solvent, the aromatic compound Ar—X, and tetramethylammonium 2,6-dimethylphenolate. The result of the reaction is a fluorinated aromatic compound having the formula Ar—F.

As shown in Scheme I, a fluorinating reagent is provided to the reaction mixture. In one embodiment, the fluorinating reagent is an aryl fluorosulfonate (also called an aryl sulfurofluoridate). An aryl fluorosulfonate is an aryl compound having a —OSO$_2$F substituent. In one instance the aryl group of the aryl fluorosulfonate is further substituted.

In another embodiment, the fluorinating reagent is a heteroaryl fluorosulfonate (also called an heteroaryl sulfurofluoridate). In one instance the heteroaryl group of the heteroaryl fluorosulfonate is further substituted. A heteroaryl fluorosulfonate is a heteroaryl compound having a —OSO$_2$F substituent.

In another embodiment, the fluorinating reagent is sulfuryl fluoride, i.e., SO$_2$F$_2$, which is a gas and commercially available as a fumigant. The sulfuryl fluoride can be dissolved into the reaction mixture, preferably by bubbling the gas into the mixture. In an embodiment, the sulfuryl fluoride is bubbled into the solvent prior to adding to the reaction mixture.

The reaction shown in Scheme I may be carried out in the presence of a solvent. Alternatively, when both the starting material and product are liquids at, for example, room temperature, the reaction may be carried out in the absence of a solvent, i.e., neat, to simplify isolation and purification of the product.

In reactions in which a solvent is employed, the solvent may be a polar aprotic solvent. Examples of suitable polar aprotic solvents include dimethyl formamide (DMF), dimethyl sulfoxide (DMSO), N-methyl-2-pyrrolidone (NMP), dimethylacetamide (DMA), 1,3-dimethyl-3,4,5,6-tetrahydro-2(1H)-pyrimidinone (DMPU), dimethylacetamide (DMA), dichloromethane (DCM), acetonitrile, ethyl acetate, hexamethylphosphoric triamide (HMPT), and 1,3-dimethyl-2-imidazolidinone (DMI).

Alternatively the solvent may be an alkoxy ether solvent. Examples of suitable alkoxy ether solvents include tetrahydrofuran (THF), diglyme, and dimethoxyethane (DME). Other suitable solvents for the reaction are a nitrile solvents. Benzonitrile is an example of a suitable nitrile solvent.

Other solvents useful in the reaction are aromatic solvents, such as, for example, toluene In certain embodiments where a solvent is employed, additional solvent may be added to the reaction mixture separate from the solvent in which the fluorinating reagent, e.g., sulfuryl fluoride, is dissolved. This additional solvent is preferably a polar aprotic solvent.

As noted above, the reaction mixture contains a tetraalkyl ammonum phenolate salt. As used herein, the term "phenolate" refers to groups of the formula

wherein
n is 0 or 1, 2, 3, 4, or 5;
Z represents 0 or S; and
each R$_1$ independently represents C$_1$-C$_6$ alkyl, C$_2$-C$_6$ alkenyl, nitro, halo, cyano, CO$_2$R$_2$ where each R$_2$ is hydrogen, C$_1$-C$_6$ alkyl, amino, (C$_1$-C$_6$ alkyl)amino, or di(C$_1$-C$_6$ alkyl)amino, aryl, or heteroaryl.

Representative examples of suitable tetraalkyl ammonium phenolate salts include compounds wherein
n is 0, and Z is S or 0;
n is 1, Z is S or O, and R$_1$ is methyl;
n is 2, Z is S or O, and each R$_1$ is methyl.

In one embodiment, the tetraalkyl ammonum phenolate salt is a tetramethylammonium 2,6-dimethylphenolate, such as, for example, one of the following:

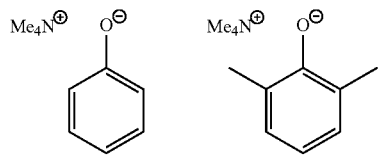

In another embodiment, the tetraalkyl ammonium phenolate salt is a tetraalkylammonium thiophenolate salt, such as, for example:

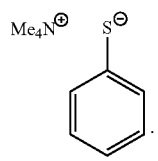

Preferably, the reaction is performed in a substantially water-free environment. Generally, as the amount of water in the reaction increases, the product yield decreases.

The reaction scheme is preferably performed at a reaction temperature of from 0 to 130° C. In one instance, the reaction temperature is from 25 to 80° C. Typically, the reaction mixture is contained in a sealed container. The reaction mixture is allowed to react for time sufficient to provide the desired product, for example 24 hours.

In one embodiment, the reaction mixture contains 3 to 10 equivalents of the fluorinating reagent, e.g., sulfuryl fluoride, in the reaction mixture, based on the amount of aromatic starting material Ar—X. In one embodiment, the reaction mixture contains 4 equivalents of fluorinating reagent, e.g., sulfuryl fluoride. In another embodiment, the reaction mixture contains 2 to 3 equivalents of tetraalkyl ammonium phenolate salt. In one instance, the reaction mixture contains 2.5 equivalents of tetraalkyl ammonium phenolate salt. These equivalents are calculated based on the molar amount of the aromatic compound Ar—X in the reaction mixture.

In one instance, the reaction mixture does not contain a catalyst. One of the benefits of the reaction scheme described herein is that the scheme proceeds without the use of a catalyst.

The methods disclosed herein are illustrated further by the following examples, which are not to be construed as limiting the disclosed subject matter in scope or spirit to the specific procedures and compounds described in them.

EXAMPLES

Example 1

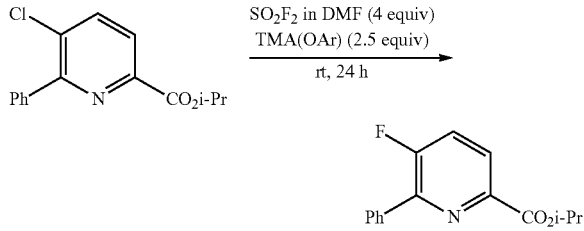

In a glovebox, iso-propyl 5-chloro-6-phenylpicolinate (0.050 mmol, 1 equiv), tetramethylammonium 2,6-dimethylphenolate (TMA(OAr)) (0.125 mmol, 2.5 equiv), and sulfuryl fluoride (0.14 M solution in DMF, 0.200 mmol, 4 equiv, prepared by bubbling sulfuryl fluoride gas through DMF) are added to a vial. DMF (0.07 mL) is added to the reaction to make the total concentration 0.033 M. The vial is sealed with a Teflon-lined cap and was allowed to stir for 24 hours at room temperature. After 24 hours, the reaction mixture is diluted with dichloromethane and an internal standard (4-fluoroanisole) is added. The crude reaction mixture is analyzed by $^{19}$F NMR spectroscopy and GCMS to indicate 98 percent yield.

Example 2

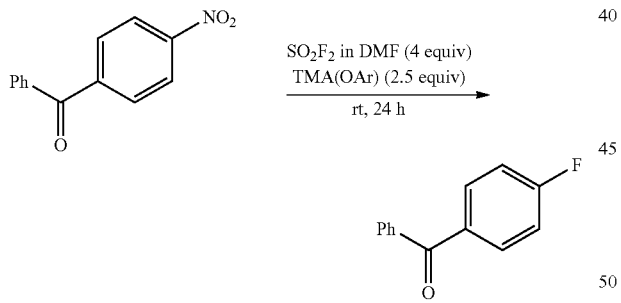

In a glovebox, 4-nitrophenyl(phenyl)methanone (0.050 mmol, 1 equiv), tetramethylammonium 2,6-dimethylphenolate (0.125 mmol, 2.5 equiv), and sulfuryl fluoride (0.14 M solution in DMF, 0.200 mmol, 4 equiv, prepared by bubbling sulfuryl fluoride gas through DMF) are added to a vial. DMF (0.07 mL) are added to the reaction to make the total concentration 0.033 M. The vial is sealed with a Teflon-lined cap and was allowed to stir for 24 hours at room temperature. After 24 hours, the reaction mixture is diluted with dichloromethane and an internal standard (4-fluoroanisole) is added. The crude reaction mixture is analyzed by $^{19}$F NMR spectroscopy and GCMS to indicate a greater than 85 percent yield.

Example 3

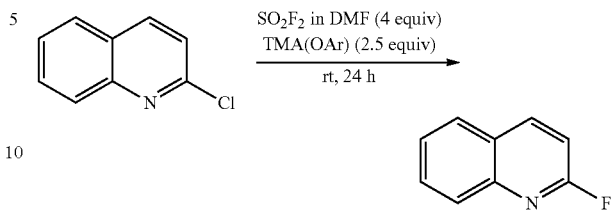

In a glovebox, 2-chloroquinoline (0.050 mmol, 1 equiv), tetramethylammonium 2,6-dimethylphenolate (0.125 mmol, 2.5 equiv), and sulfuryl fluoride (0.14 M solution in DMF, 0.200 mmol, 4 equiv, prepared by bubbling sulfuryl fluoride gas through DMF) are added to a vial. DMF (0.07 mL) are added to the reaction to make the total concentration 0.033 M. The vial is sealed with a Teflon-lined cap and was allowed to stir for 24 hours at room temperature. After 24 hours, the reaction mixture is diluted with dichloromethane and an internal standard (4-fluoroanisole) is added. The crude reaction mixture is analyzed by $^{19}$F NMR spectroscopy and GCMS to indicate a greater than 78 percent yield.

Example 4

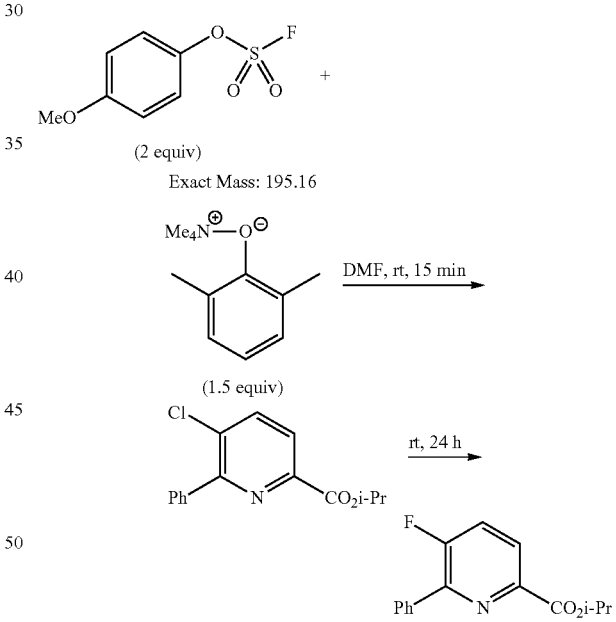

In a glovebox, 4-methoxyphenyl sulfurofluoridate (0.167 mmol, 2 equiv), and tetramethylammonium 2,6-dimethylphenolate (0.125 mmol, 1.5 equiv), are added to a vial. DMF (0.07 mL) are added to the reaction to make the total concentration 0.033 M. The vial is sealed with a Teflon-lined cap and was allowed to stir for 15 minutes at room temperature. Iso-propyl 5-cholor-6-phenylpicolinate (0.083 mmol, 1 equivalent) is added to the vial and is allowed to stir for 24 hours. After 24 hours, the reaction mixture is diluted with dichloromethane and an internal standard (4-fluoroanisole) is added. The crude reaction mixture is analyzed by $^{19}$F NMR spectroscopy and GCMS to indicate a greater than 82 percent yield.

Example 5

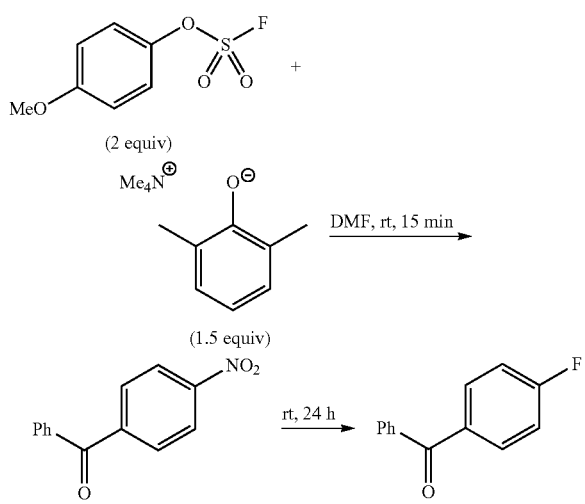

In a glovebox, 4-methoxyphenyl sulfurofluoridate (0.167 mmol, 2 equiv), and tetramethylammonium 2,6-dimethylphenolate (0.125 mmol, 1.5 equiv), are added to a vial. DMF (0.07 mL) are added to the reaction to make the total concentration 0.033 M. The vial is sealed with a Teflon-lined cap and was allowed to stir for 15 minutes at room temperature. (4-nitrophenyl)(pyenyl)methanone (0.083 mmol, 1 equivalent) is added to the vial and is allowed to stir for 24 hours. After 24 hours, the reaction mixture is diluted with dichloromethane and an internal standard (4-fluoroanisole) is added. The crude reaction mixture is analyzed by $^{19}$F NMR spectroscopy and GCMS to indicate a quantitative yield.

Example 6

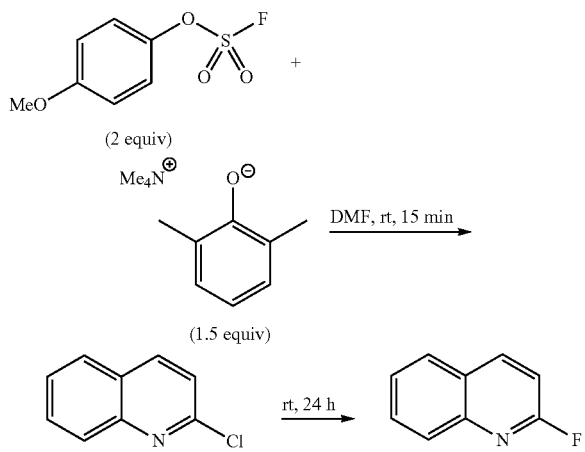

In a glovebox, 4-methoxyphenyl sulfurofluoridate (0.167 mmol, 2 equiv), and tetramethylammonium 2,6-dimethylphenolate (0.125 mmol, 1.5 equiv), are added to a vial. DMF (0.07 mL) are added to the reaction to make the total concentration 0.033 M. The vial is sealed with a Teflon-lined cap and was allowed to stir for 15 minutes at room temperature. 2-chloroquinoline (0.083 mmol, 1 equivalent) is added to the vial and is allowed to stir for 24 hours. After 24 hours, the reaction mixture is diluted with dichloromethane and an internal standard (4-fluoroanisole) is added. The crude reaction mixture is analyzed by $^{19}$F NMR spectroscopy and GCMS to indicate a greater than quantitative yield.

The invention and the manner and process of making and using it, are now described in such full, clear, concise and exact terms as to enable any person skilled in the art to which it pertains, to make and use the same. It is to be understood that the foregoing describes preferred embodiments of the invention and that modifications may be made therein without departing from the spirit or scope of the invention as set forth in the claims. To particularly point out and distinctly claim the subject matter regarded as invention, the following claims conclude this specification.

What is claimed is:

1. A fluorination method comprising:
   providing a solvent to a reaction mixture;
   providing a fluorinating reagent to the reaction mixture;
   providing a compound having the formula Ar—X to the reaction mixture;
   wherein:
      Ar is aryl, substituted aryl, heteroaryl or substituted heteroaryl, and
      X is Cl, Br, I or NO$_2$;
   providing a tetraalkyl ammonium phenolate salt to the reaction mixture; and
   reacting under conditions sufficient to provide a species having the formula Ar—F.

2. The fluorination method of claim 1, wherein the solvent is a polar aprotic solvent.

3. The fluorination method of claim 1, wherein Ar is iso-propyl 5-chloro-6-phenylpicolinate, 2-chloroquinoline, or (4-nitrophenyl)(phenyl)methanone.

4. The fluorination method of claim 1, wherein the reaction temperature is from 0 to 130 degrees C.

5. The fluorination method of claim 1, wherein the reaction mixture includes 1 equivalent of the Ar—X, 2 to 3 equivalents of tetramethylammonium 2,6-dimethylphenolate, and 3 to 10 equivalents of the fluorinating reagent.

6. The fluorination method of claim 2, wherein the polar aprotic solvent comprises DMF, NMP, DMSO, DMPU, or DMA.

7. The fluorination method of claim 4, wherein the reaction temperature is from 25 to 130 degrees C.

8. The fluorination method of claim 1, wherein the tetraalkyl ammonium phenolate salt is tetramethylammonium 2,6-dimethylphenolate.

9. The fluorination method of claim 1, wherein the reaction mixture does not contain a catalyst.

10. The fluorination method of claim 1, wherein the fluorinating reagent is sulfuryl fluoride, an aryl fluorosulfonate or a heteroaryl fluorosulfonate.

11. The fluorination method of claim 2, wherein Ar is iso-propyl 5-chloro-6-phenylpicolinate, 2-chloroquinoline, or (4-nitrophenyl)(phenyl)-methanone.

12. The fluorination method of claim 11, wherein the reaction temperature is from 0 to 130 degrees C.

13. The fluorination method of claim 12, wherein the reaction mixture includes 1 equivalent of the Ar—X, 2 to 3 equivalents of tetramethylammonium 2,6-dimethylphenolate, and 3 to 10 equivalents of the fluorinating reagent.

14. The fluorination method of claim 13, wherein the polar aprotic solvent comprises DMF, NMP, DMSO, DMPU, or DMA.

15. The fluorination method of claim 2, wherein the reaction temperature is from 0 to 130 degrees C.

16. The fluorination method of claim 15, wherein the reaction mixture includes 1 equivalent of the Ar—X, 2 to 3 equivalents of tetramethylammonium 2,6-dimethylphenolate, and 3 to 10 equivalents of the fluorinating reagent.

17. The fluorination method of claim 16, wherein the polar aprotic solvent comprises DMF, NMP, DMSO, DMPU, or CDMA.

\* \* \* \* \*